United States Patent [19]
Berg

[11] Patent Number: 5,167,774
[45] Date of Patent: Dec. 1, 1992

[54] DEHYDRATION OF ACETIC ACID BY EXTRACTIVE DISTILLATION

[75] Inventor: Lloyd Berg, 1314 South Third Ave., Bozeman, Mont. 59715

[73] Assignee: Lloyd Berg, Bozeman, Mont.

[21] Appl. No.: 828,667

[22] Filed: Feb. 6, 1992

[51] Int. Cl.$^5$ .................. B01D 3/40; C07C 51/44; C07C 53/08
[52] U.S. Cl. ........................... 203/16; 203/57; 203/58; 203/60; 562/608
[58] Field of Search ............ 203/16, 57, 58, 60; 562/608

[56] References Cited

U.S. PATENT DOCUMENTS

| | | | |
|---|---|---|---|
| 1,624,811 | 4/1927 | Suida | 562/608 |
| 3,951,755 | 4/1976 | Sartorius et al. | 203/60 |
| 4,576,683 | 3/1986 | Cohen | 203/16 |
| 4,642,166 | 2/1987 | Berg et al. | 203/15 |
| 4,670,105 | 6/1987 | Berg et al. | 203/60 |
| 4,729,818 | 3/1988 | Berg | 203/16 |
| 4,735,690 | 4/1988 | Berg et al. | 203/15 |

*Primary Examiner*—Wilbur Bascomb, Jr.

[57] ABSTRACT

Acetic acid cannot be easily removed from acetic acid - water mixtures by distillaton because of the closeness of their boiling points and the deviation from ideal solution behavior. Acetic acid can be readily removed from the mixtures containing it and water by using extractive distillation. Typical effective agents are sulfolane and adiponitrile.

1 Claim, No Drawings

DEHYDRATION OF ACETIC ACID BY EXTRACTIVE DISTILLATION

FIELD OF THE INVENTION

This invention relates to a method for dehydrating acetic acid using certain higher boiling liquids as the agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boils twenty Centigrade degrees or more than the lowest boiling component.

At the bottom of a continuous column, the less volatile components of the close boiling mixture and the extractive agent are continuously removed from the column. The usual methods of separation of these two components are the use of another rectification column, cooling and phase separation or solvent extraction.

Currently there are at least four commercial ways to manufacture acetic acid. The fermentation of fruit (apples) or wood waste are the oldest. The reaction of acetylene with water to form acetaldehyde followed by air oxidation is still in use. Fermentation of ethanol to acetic acid is used when cheap ethanol is available. The reaction of methanol with carbon monoxide in aqueous solution is currently in favor because of cheap methanol. The air oxidation of butane to give a multitude of products, approximately forty, including acetic acid is currently attractive. All of these processes present the problem of separating water from acetic acid. Acetic acid boils at 118° C., water at 100° C. but although these two do not form an azeotrope, they are far from being an ideal mixture. The separation of water from acetic acid by distillation becomes especially difficult at high concentrations of acetic acid. Currently they are separated by azeotropic distillation. In this process, the azeotrope former is a compound such as butyl acetate which takes the water off overhead as a two-phase azeotrope. The water is decanted and the butyl acetate recycled. Many azeotrope forming compounds have been suggested for this separation. Anything that forms a two-phase azeotrope with water, e.g. is insoluble in water, is soluble in acetic acid but does not form an azeotrope with acetic acid, will accomplish this mode of separation.

Extractive distillation would be an attractive method of effecting the separation of acetic acid from water if agents can be found that (1) will create a large apparent relative volatility between water and acetic acid and (2) are easy to recover from acetic acid, that is, form no azeotrope with acetic acid and boil sufficiently above acetic acid to make the separation by rectification possible with only a few theoretical plates.

Extractive distillation typically requires the addition of an equal amount to twice as much extractive agent as the acetic acid-water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents requires if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with acetic acid otherwise it will form a two-phase azeotrope with acetic acid in the recovery column and some other method of separation will have to be employed.

R. Sartorius & H. Stapf, U.S. Pat. No. 3,951,755, Apr. 20, 1976 described an extractive distillation process to dehydrate acetic acid using N-methyl acetamide. Mercer, U.S. Pat. No. 2,588,268 described the use of isophorone as the agent in the dehydration of acetic acid by extractive distillation. Soviet Union Pat. 445,645 described an azeotropic distillation process to separate acetic acid from water using toluene as the agent. Berg, U.S. Pat. No. 4,729,818 described an extractive distillation process for dehydrating acetic acid using higher boiling fatty acids.

OBJECTIVE OF THE INVENTION

The object of this invention is to provide a process or method of extractive distillation that will enhance the relative volatility of water from acetic acid in their separation in a rectification column. It is a further object of this invention to identify organic compounds which in addition to the above constraints, are stable, can be separated from acetic acid by rectification with relatively few theoretical plates and can be recycled to the extractive distillation column and reused with little decomposition.

SUMMARY OF THE INVENTION

The objects of this invention are provided by a process for separating acetic acid from water which entails the use of certain nitrogenous or sulfur containing organic compounds.

TABLE 1

| Effective Extractive Distillation Agents | |
|---|---|
| Compounds | Relative Volatility |
| Dimethylsulfoxide | 9.0 |
| Sulfolane | 2.5 |
| Dimethylformamide | 10+ |
| Dimethylcetamide | 10+ |
| Adiponitrile | 7.1 |

TABLE 2

Data From Run Made In Rectification Column

| Agent | Time hrs. | Temp. °C. | Weight % Water | Weight % Acetic Acid | Relative Volatility |
|---|---|---|---|---|---|
| Sulfolane | 1 | Overhead 89 | 99.8 | 0.2 | 2.2 |
|  |  | Bottoms 115 | 60.1 | 39.9 |  |

DETAILED DESCRIPTION OF THE INVENTION

I have discovered that certain nitrogenous or sulfur containing compounds will greatly improve the relative volatility of water to acetic acid and permit the separation of pure water from acetic acid by rectification when employed as the agent in extractive distillation. Table 1 lists the compounds that I have found to be effective. The data in Table 1 was obtained in a vapor-liquid equilibrium still. The compounds which are effective are dimethylsulfoxide, sulfolane, dimethylformamide, dimethylacetamide and adiponitrile.

One of the compounds, sulfolane, listed in Table 1 and whose relative volatility had been determined in the vapor-liquid equilibrium still, was then evaluated in a glass perforated plate rectification column possessing 7.3 theoretical plates and the results listed in Table 2 and Example 2.

THE USEFULNESS OF THE INVENTION

The usefulness or utility of this invention can be demonstrated by referring to the data presented in Table 1. All of the successful extractive distillation agents show that acetic acid and water can be separated from each other by means of distillation in a rectification column and that the improvement in the ease of separation as measured by relative volatility is considerable. The data also show that the most attractive agents will operate at a boilup rate low enough to make this a useful and efficient method of recovering high purity acetic acid from any mixture with water. The stability of the compounds used and the boiling point difference is such that complete recovery and recycle is obtainable by a simple distillation and the amount required for make-up is small.

WORKING EXAMPLES

EXAMPLE 1

Thirty-five grams of acetic acid, 35 grams of water and 60 grams of adiponitrile were charged to an Othmer type vapor-liquid equilibrium still and refluxed for six hours. Analysis of the vapor and liquid by gas chromatography gave vapor composition of 88.8% water, 11.2% acetic acid and a liquid composition of 52.6% water, 47.4% acetic acid. This indicates a relative volatility of 7.1.

EXAMPLE 2

A glass perforated plate rectification column was calibrated with ethyl benzene and p-xylene which mixture possesses a relative volatility of 1.06 and found to have 7.3 theoretical plates. A solution comprising 100 grams of acetic acid and 150 grams of water was placed in the stillpot and heated. When refluxing began, an extractive agent consisting of sulfolane was pumped into the column at a rate of 20 ml/min. The temperature of the extractive agent as it entered the column was 90° C. After establishing the feed rate of the extractive agent, the heat input to the acetic acid and water in the stillpot was adjusted to give a total reflux rate of 40 ml/min. After one hour of operation, the overhead and bottoms samples were collected and analysed. The overhead composition was 99.8% water, 0.2% acetic acid and the bottoms composition was 60.1% water, 39.9% acetic acid. This gave an average relative volatility of 2.2 using the Fenske equation for a 7.3 theoretical plate column.

I claim:

1. A method for recovering acetic acid from a mixture of acetic acid and water which comprises distilling a mixture of acetic acid and water in a rectification column in the presence of about one to two parts of and extractive agent per part of acetic acid-water mixture, recovering water as overhead product and obtaining the acetic acid and the extractive agent from the stillpot, wherein said extractive agent consists of dimethylsulfoxide.

* * * * *